(12) United States Patent
Ekdahl et al.

(10) Patent No.: US 9,925,323 B2
(45) Date of Patent: Mar. 27, 2018

(54) APPARATUS FOR EXTRACORPOREAL BLOOD TREATMENT AND METHOD OF OPERATION

(75) Inventors: Olof Ekdahl, Lund (SE); Bjorn Ericson, Lund (SE)

(73) Assignee: Gambro Lundia AB, Lund (SE)

(*) Notice: Subject to any disclaimer, the term of this patent is extended or adjusted under 35 U.S.C. 154(b) by 1050 days.

(21) Appl. No.: 13/516,824

(22) PCT Filed: Dec. 15, 2010

(86) PCT No.: PCT/EP2010/069705
§ 371 (c)(1),
(2), (4) Date: Aug. 29, 2012

(87) PCT Pub. No.: WO2011/080071
PCT Pub. Date: Jul. 7, 2011

(65) Prior Publication Data
US 2012/0318740 A1     Dec. 20, 2012

Related U.S. Application Data

(60) Provisional application No. 61/287,218, filed on Dec. 17, 2009.

(51) Int. Cl.
*A61M 1/36* (2006.01)

(52) U.S. Cl.
CPC ........ *A61M 1/3626* (2013.01); *A61M 1/3643* (2013.01); *A61M 1/3644* (2014.02); *A61M 1/3656* (2014.02); *A61M 2205/3306* (2013.01); *A61M 2205/3331* (2013.01); *A61M 2205/705* (2013.01)

(58) Field of Classification Search
CPC ............................................. A61M 2005/705
See application file for complete search history.

(56) References Cited

U.S. PATENT DOCUMENTS

| | | | |
|---|---|---|---|
| 3,607,117 A * | 9/1971 | Shaw et al. | 422/111 |
| 3,946,731 A * | 3/1976 | Lichtenstein | 604/66 |
| 4,797,655 A | 1/1989 | Orndal et al. | |
| 5,382,227 A | 1/1995 | Riquier | |
| 5,394,732 A * | 3/1995 | Johnson et al. | 73/19.1 |
| 5,472,614 A * | 12/1995 | Rossi | 210/646 |
| 5,591,344 A * | 1/1997 | Kenley et al. | 210/636 |
| 5,776,345 A | 7/1998 | Truitt et al. | |
| 6,806,947 B1 | 10/2004 | Ekdahl et al. | |
| 2002/0104800 A1 | 8/2002 | Colins et al. | |
| 2003/0128126 A1* | 7/2003 | Burbank et al. | 340/605 |

(Continued)

FOREIGN PATENT DOCUMENTS

EP     1 892 001 A1     2/2008

*Primary Examiner* — Krishnan S Menon
*Assistant Examiner* — Bradley R Spies
(74) *Attorney, Agent, or Firm* — K&L Gates LLP

(57) ABSTRACT

Systems and methods for monitoring the presence of blood in an extracorporeal blood circuit are disclosed. A control unit, which is connected to a blood detector and to one or several pressure sensors, determines whether blood is present in the membrane device based on the differential pressure there over and generates a signal if the presence of blood as detected by the blood detector and the presence of blood as determined based on the differential pressure value do not coincide with each other.

28 Claims, 6 Drawing Sheets

(56) References Cited

U.S. PATENT DOCUMENTS

2006/0213835 A1   9/2006  Nimura et al.
2006/0282036 A1  12/2006  Gatti et al.
2006/0293601 A1* 12/2006  Lane et al. .................... 600/495
2008/0154170 A1   6/2008  Lannoy
2009/0101576 A1   4/2009  Rohde et al.
2009/0152200 A1   6/2009  Lannoy

* cited by examiner

APPARATUS FOR EXTRACORPOREAL BLOOD TREATMENT AND METHOD OF OPERATION

RELATED APPLICATION

This application is a U.S. National Phase of PCT/EP2010/069705 having an international filing date of 15 Dec. 2010, and claims priority to U.S. provisional application 61/287,218 filed 17 Dec. 2009 and Swedish patent application 0950968-8 filed 17 Dec. 2009, the entirety of all of these applications are incorporated by reference.

TECHNICAL FIELD

The invention relates to an apparatus for extracorporeal blood treatment, and a method for operating such an apparatus.

BACKGROUND

There are several types of treatments in which blood is extracted in an extracorporeal blood circuit. Such treatments involve, for example, haemodialysis, haemofiltration, haemodiafiltration, plasmapheresis, blood component separation, blood oxygenation, etc. Normally, blood is removed from a blood vessel at an access site and returned to the same blood vessel or at another location in the body.

In the case of haemodialysis, a treatment fluid (also referred to as a dialysis fluid) is made approximately isotonic with a patient's blood, each flowing on each side of a semi-permeable membrane of a membrane device (referred to as a dialyzer), so that, during the diffusive transfer which is established across the membrane in the case of substances having different concentrations on either side of the membrane, the impurities in the blood (urea, creatinine, etc.) migrate from the blood into the treatment fluid. The electrolyte concentration of the treatment fluid is also generally chosen so as to correct for the electrolyte concentration of the patient's blood.

In treatment by haemodiafiltration, a convective transfer by ultrafiltration, resulting from a positive pressure difference created between the blood side and the treatment fluid side of the membrane, is added to the diffusive transfer obtained by dialysis.

An apparatus for extracorporeal blood treatment includes a stage in which the disposable extracorporeal blood circuit is coupled to a treatment control monitor (for example a dialysis monitor). This stage, which is prepared before connecting up the extracorporeal blood circuit to the patient, includes connection of the blood transport lines (in general an arterial line for blood removal from the patient, and a venous line for blood return to the patient) to the membrane device for blood treatment, which in turn is connected up to the treatment fluid supply circuit and to a used treatment fluid discharge circuit.

The semi-permeable membrane of the membrane device divides a blood compartment, connected to the blood transport lines, and a fluid compartment, connected to the supply and discharge circuits. The blood transport lines are further coupled to a sensor and actuator system equipped on the treatment control monitor, which system normally comprises means for blood circulation, pressure sensors, air bubble sensor, one or more circuit blocking clamps, blood detector, etc.

Before connection of the extracorporeal blood circuit to the patient's vascular system, a priming stage is usually performed of the blood transport lines and the membrane device, which then are filled with a priming liquid (usually an isotonic saline solution or another patient-isotonic liquid). The priming stage performs the function of expelling air, filling and rinsing.

SUMMARY

According to an aspect of the present invention there is provided a system for monitoring the presence of blood in an extracorporeal blood circuit. The system comprises a blood detector designed to receive a portion of the extracorporeal blood circuit and to detect the presence of blood therein, one or several pressure sensors designed to provide a differential pressure value which represents the pressure between the pressure on a first and second side of the blood side of a membrane device, and a control unit, the blood detector and the pressure sensors being connected to the control unit. The control unit is designed to determine the presence of blood in the membrane device based on the differential pressure value and to generate a signal if the presence of blood as detected by the blood detector and the presence of blood as determined based on the differential pressure value do not coincide with each other.

According to another aspect of the present invention the control unit is designed to prevent the generation of the signal for a period of time.

According to yet another aspect of the present invention the system is integrated in a treatment control monitor for dialysis treatment.

According to yet another aspect of the present invention the control unit is designed to test the blood detector before blood is allowed to enter the extracorporeal blood circuit at the position where the blood detector is located. The control unit initiates the monitoring of the presence of blood in the blood circuit after the blood detector has been found to operate correctly.

According to other aspects of the present invention, there is provided methods of monitoring the presence of blood in an extracorporeal blood circuit corresponding to the aforementioned systems.

An advantage, in respect of some embodiments of the present invention, is that the presence of blood in the extracorporeal blood circuit is determined with a high degree of certainty since two independent means and methods are used in the process.

An further advantage, in respect of some embodiments of the present invention, is that the proper connection of the extracorporeal blood circuit to the blood detector can be determined with high degree of certainty.

A further advantage, in respect of some embodiments of the present invention, is that the risks of an incorrect treatment of the patient, incorrect stop of the treatment and incorrect generation of alarms, and/or that blood from the patient may not be correctly returned to the patient, as discussed above, are significantly reduced.

DETAILED DESCRIPTION

Figure 1:
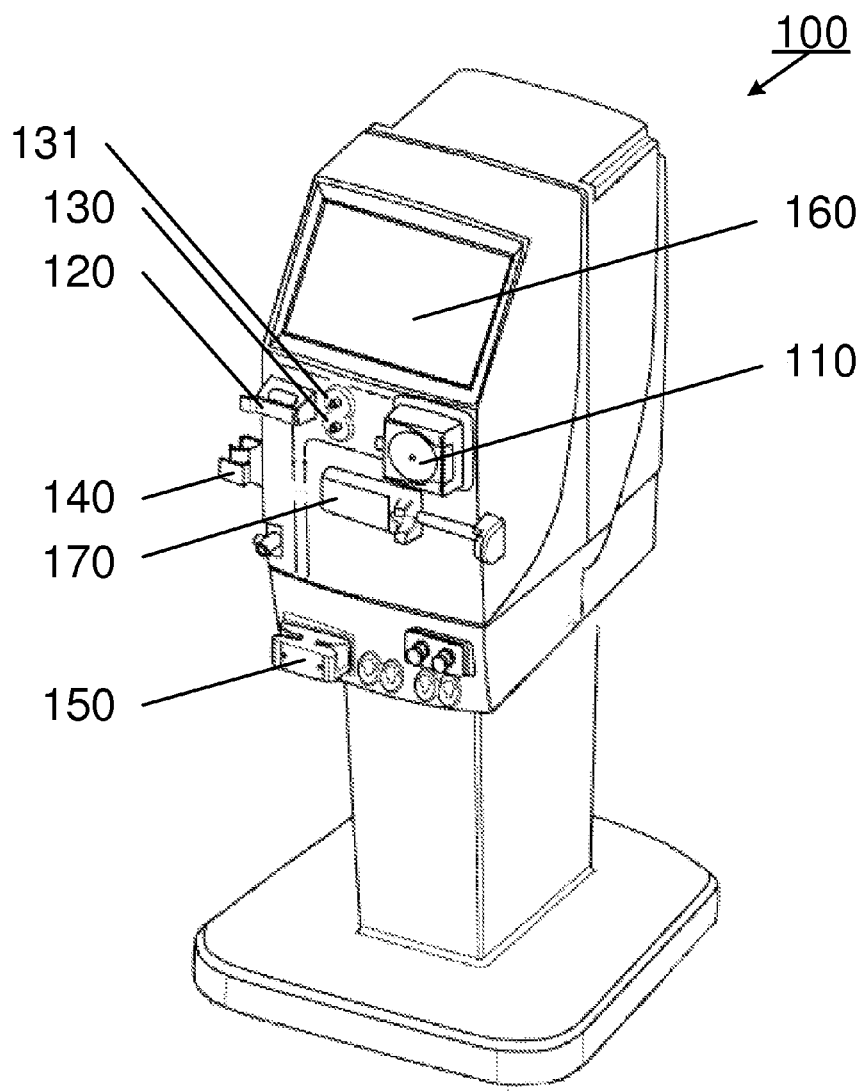
FIG. 1 illustrates a treatment control monitor.

FIG. 1 illustrates a treatment control monitor 100. The treatment control monitor together with the disposable extracorporeal blood circuit (not shown) forms the apparatus for extracorporeal blood treatment. The treatment control monitor 100 comprises a blood pump 110. The blood pump 110 may be a peristaltic pump and it may be driven by an electric step motor. The treatment control monitor 100 further comprises a holder for a venous drip chamber 120, input ports 130, 131 for pressure sensors (not shown), a membrane device holder 140 to which the membrane device can be mounted, a blood detector and double clamp device 150, and a display and input device 160.

The treatment control monitor 100 may comprise other functional elements such as a syringe pump 170 used for distributing an anti-coagulant substance, a treatment fluid pump for pumping the treatment fluid through the membrane device, arrangements for preparing the treatment fluid (for example from a water source and one or several dry concentrates), etc.

When setting up the apparatus for extracorporeal blood treatment, the disposable extracorporeal blood circuit is mounted on the treatment control monitor 100 by an operator (which may be the patient for example in the case of home haemodialysis). The membrane device is placed in the membrane device holder 140 and the venous drip chamber is placed in the venous drip chamber holder 120. The blood transport lines, which comprises an withdrawal line for blood removal from the patient, and a return line for blood return to the patient, is connected to the opposite sides of the blood side of the membrane device and is also mounted onto the blood pump 110, and connected to the blood detector and double clamp device 150. The return line is connected to the blood detector and the adjacent clamp whereas the withdrawal line is connected to the other clamp. Pressure measurement connections are connected to the input ports 130, 131 for pressure sensors. The blood transport lines need also to be connected to the venous drip chamber in case the venous drip chamber is not made part of blood transport line itself.

Additionally, the treatment fluid circuit is mounted on the treatment control monitor 100 and connected to the treatment fluid side of the membrane device. Appropriate connections are also made to the treatment fluid supply circuit and the used treatment fluid discharge circuit.

In operation, the venous drip chamber substantially removes air bubbles from the blood line before the blood is returned to the patient. The two clamps allow the treatment control monitor to open and close the fluid flow in the withdrawal and return blood lines, respectively.

Before connection of the extracorporeal blood circuit to the patient's vascular system, a priming stage is usually performed of the blood transport lines and the membrane device. The priming liquid is usually an isotonic saline solution or another patient-isotonic liquid. During the priming stage, extracorporeal blood circuit is filled with priming liquid for example by allowing the priming liquid to enter the blood transport lines at the withdrawal line and transporting it through the withdrawal line, the membrane device and the return line by operating the blood pump.

After the filling of the extracorporeal blood circuit with priming liquid, the patient's vascular system is connected to the withdraw line for example by means of a first needle. Generally there are two alternatives for the sequence of events in conjunction with the connection of the return line. According to a first alternative, the return line is connected to the patient's vascular system at the same time as the withdrawal line is connected. When the blood pump is set in operation, the priming liquid will be entering the patient's vascular system. At the same time blood will be filling up the extracorporeal blood circuit and after reaching the return line be returned to the patient. According to a second alternative, the priming liquid is pumped out from the blood transport line into a drain while, at the same time, blood is filling up the extracorporeal blood circuit. In this alternative, the return line is not connected to the patient's vascular system, which is done for example by a second needle, until the blood has reached the return line, preferably, the end of the return line.

It is generally important for the treatment control monitor 100 to have information whether there is blood in the return line of the extracorporeal blood circuit. The detection of blood in the return line is done by the blood detector of the blood detector and double clamp device 150. When priming is conducted according to the first alternative (as mentioned above), the detection of blood in the return line indicates to the treatment control monitor 100 that the actual treatment of the patient may be initiated. If the blood detector fails to correctly detect blood in the return line then the patient may receive an incorrect treatment. When priming is conducted according to the second alternative (as mentioned above), the detection of blood in the return line indicates to the treatment control monitor 100 that the blood pump 110 should be stopped, and possibly that the return line clamp should be closed, since the actual treatment of the patient cannot be initiated until the return path to the patient's vascular system has been established. If the blood detector fails to correctly detect blood in the return line in this case then the patient may receive an incorrect treatment or the patient's blood may be pumped out through a non-connected return line as the blood pump is not stopped and the return line clamp is not closed.

During the actual treatment of the patient, it is also important for the treatment control monitor 100 to have information whether there is blood in the return line. If no blood is detected in the return line this may indicate that there is a leakage in the blood transport line and/or the membrane device, that there is a kink in the blood transport line, and/or that the first needle (through which blood is withdrawn) has been dislodged. Under those conditions, the treatment control monitor 100 will normally stop the treatment (stop the blood pump 110 and close the withdrawal line clamp and the return line clamp) and generate an alarm. If the blood detector fails to correctly detect blood in the return line then the treatment control monitor 100 will incorrectly stop the treatment and generate a false alarm.

After the actual treatment of the patient, the withdrawal line clamp is closed and the withdrawal line is disconnected from the patient. The withdrawal line is connected to a replacement liquid source, the withdrawal line clamp is reopened and the blood pump 110 is again set in operation. The replacement liquid will be filling the blood transport line and the membrane device while, at the same time, the blood remaining in the extracorporeal blood circuit is being returned to the patient.

Again, it is important for the treatment control monitor 100 to have information whether there is blood in the return line. When blood is no longer detected, it is an indication to the treatment control monitor 100 that the remaining blood has been returned to the patient and, as a consequence, the blood pump 110 should be stopped and the return line clamp should be closed. At this stage the patient may be disconnected from the return line. If the blood detector fails to correctly detect blood in the return line then the treatment control monitor 100 may fail to return the patient's blood.

Figure 2:
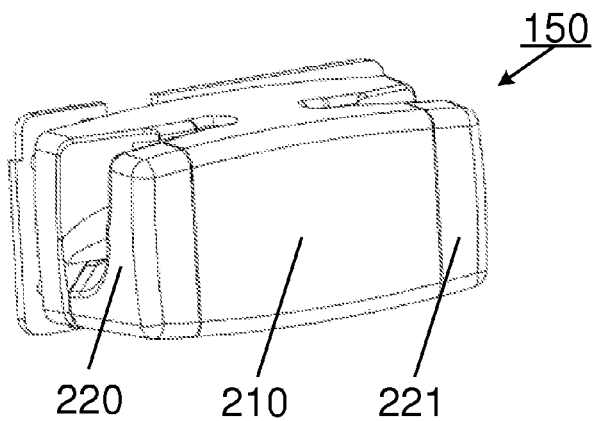
FIG. 2 illustrates a blood detector and double clamp device.
Figure 3:
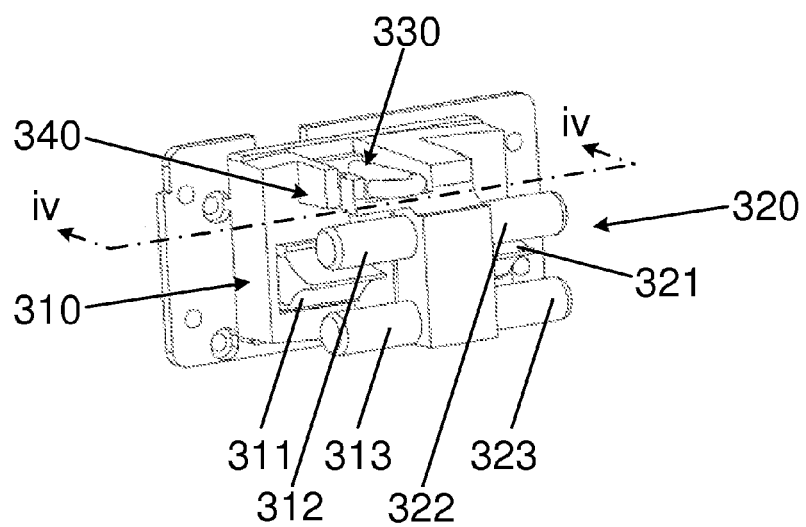
FIG. 3 illustrates the blood detector and double clamp device of FIG. 2 without housing and locking members.
Figure 4:
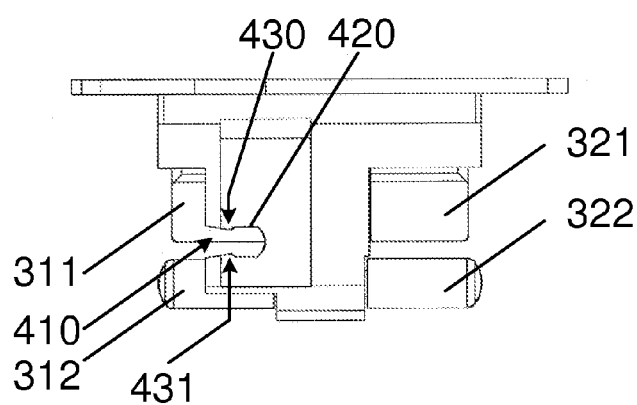
FIG. 4 illustrates a cross-sectional view along iv-iv of the blood detector and double clamp device of FIG. 3.

FIGS. 2 to 4 illustrate a blood detector and double clamp device 150. The device comprises an housing 210, a first movable locking member 220 and a second movable locking member 221. The first and second moving locking members may be folded aside when a tube (not shown) is introduced into the first and second clamp, respectively.

FIG. 3 illustrates the blood detector and double clamp device 150 when the housing 210 and the first and second locking members 220, 221 have been dismantled. A first clamp 310 and a second clamp 320 are now visible. The first clamp 310 comprises a first movable clamp element 311 and a first and a second support element 312, 313 having cylindrical forms. Similarly, the second clamp 320 comprises a second movable clamp element 321 and a third and a fourth support element 322, 323 having cylindrical forms. In operation, when a flexible tube is placed between the clamp element and the support elements, the flexible tube will be substantially closed when the movable clamp element is made to be placed in a position close to the support elements and open when the clamp element is made to be placed in a position away from the support elements.

FIG. 3 further illustrates a blood detector 330 and a tube guiding element 340. The functional elements of the blood detector may comprise a light source and a light detector, positioned such that the light from the light source is lead across the tube and thereafter received by the detector. Light in this context is meant to include ultraviolet and infrared light. Blood detectors of this kind are disclosed in U.S. Pat. No. 4,797,655 and U.S. Pat. No. B1 6,806,947 which are hereby incorporated by reference. Alternatively, the functional elements of the blood detector may comprise an ultrasonic transmitter and detector making use of an acoustic signal going across the tube.

FIG. 4 illustrates a cross-sectional view along iv-iv (as is shown in FIG. 3) of the blood detector and double clamp device 150. The tube guiding element 340 comprises a gap 410 for receiving the flexible tube, an opening 420 for holding the flexible tube in its connected position and a first and a second locking member 430, 431 for retaining a connected tube in the connected position.

The guiding element 340 is configured to, when the tube is correctly connected, to secure the tube in a position in order to enable proper function of the blood detector 330 and the first clamp 310.

The correct operation of the blood detector 330 will depend on to what extent the tube is hold in a correct position vis-à-vis the functional elements of the blood detector. The correct position is in turn dependent on that the tube is correctly connected by the operator, that the guiding element is not damaged and correctly holds and locks the tube in its correct position, and that the tube is not damaged and have the right qualities in order to correctly interact with the guiding element.

If any of the above is not fulfilled, the blood detector may not operate correctly, which, as is explained above, is important in order for the treatment control monitor 100 to operate correctly. The consequences may result in an incorrect treatment of the patient, incorrect stop of the treatment and incorrect generation of an alarm, and/or that blood from the patient may not be correctly returned to the patient.

It should be noted that the aforementioned situation is not changed by the use of discrete components (that is, the use of a separate blood detector and a separate or double clamp device) instead of the blood detector and double clamp device 150 as has been disclosed above. The blood detector may comprise one or several guiding elements, the guiding element(s) may be formed as a foldable lid with a snap function. In any case, there is always a risk that the blood detector fails to properly hold and secure the tube and thereby secure proper operation of the blood detector due to incorrect connection by the operator.

Generally, the blood detector may be configured to receive any suitable portion of the extracorporeal blood circuit and the guiding element(s) may take any form as long as it (they) fulfil the function of securing the portion of the extracorporeal blood circuit received by the blood detector in order to enable the proper function of the blood detector.

The correct operation may also fail if the blood detector is damaged and/or there are defects in the functional elements or associated circuits (e.g. transmitter and receiver circuits) of the blood detector.

Figure 5:
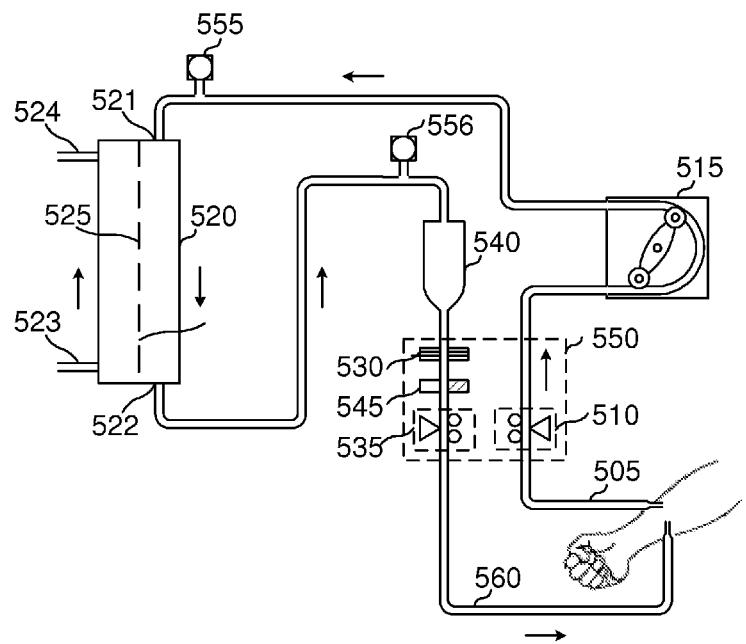
FIG. 5 shows a schematic diagram of an extracorporeal blood circuit illustrating an embodiment of the present invention.

FIG. 5 shows a schematic diagram of an extracorporeal blood circuit illustrating an embodiment of the present invention. A withdrawal line 505 is connected to a withdrawal line clamp 510 followed by a blood pump 515 before it is connected to a first input 521 on the blood side of a membrane device 520. The membrane device comprises a semi-permeable membrane 525 illustrated by a dashed line. A return line 560 is connected to a first output 522 of the blood side of the membrane device 520 followed by a blood detector 530 and a return line clamp 535. The return line comprises a venous drip chamber 540 which is located such that it appears between the membrane device and the blood detector 530. The return line 560 is also connected to a guiding element 545 which is made part of the blood detector 530 or located in its vicinity. As is explained above, the function of the guiding element 545 is to secure the portion of the extracorporeal blood circuit to be received by the blood detector in a position vis-à-vis the functional elements of the blood detector such that the blood detector may properly detect the presence of blood in the return line 560. The withdrawal line 505 is also connected to a first pressure sensor 555 and the return line 560 is also connected to a second pressure sensor 556. Such connections may be done by means of input ports for pressure sensors as discussed in reference to FIG. 1.

As is indicated in FIG. 5, the blood detector 530, the guiding element 545, the withdrawal line clamp 510 and the return line clamp 535 may be integrated into a blood detector and double clamp device 550. An example of such an integrated blood detector and double clamp device has been disclosed above in relation to FIGS. 2 to 4.

A second input 523 and a second output 524 of the treatment side of the membrane device are also illustrated in FIG. 5. The second input 523 and second output 524 are connected up to the treatment fluid supply circuit and to a used treatment fluid discharge circuit, respectively (not shown) in a manner known in the art.

In FIG. 5, the patient's vascular system is connected to the withdrawal line and the return line, respectively. This is generally not the case during the priming stage, that is, when the blood transport lines and the membrane are filled with priming liquid. The priming liquid may be allowed to enter the withdrawal line through for example the withdrawal line needle or a separate line.

Figure 6:
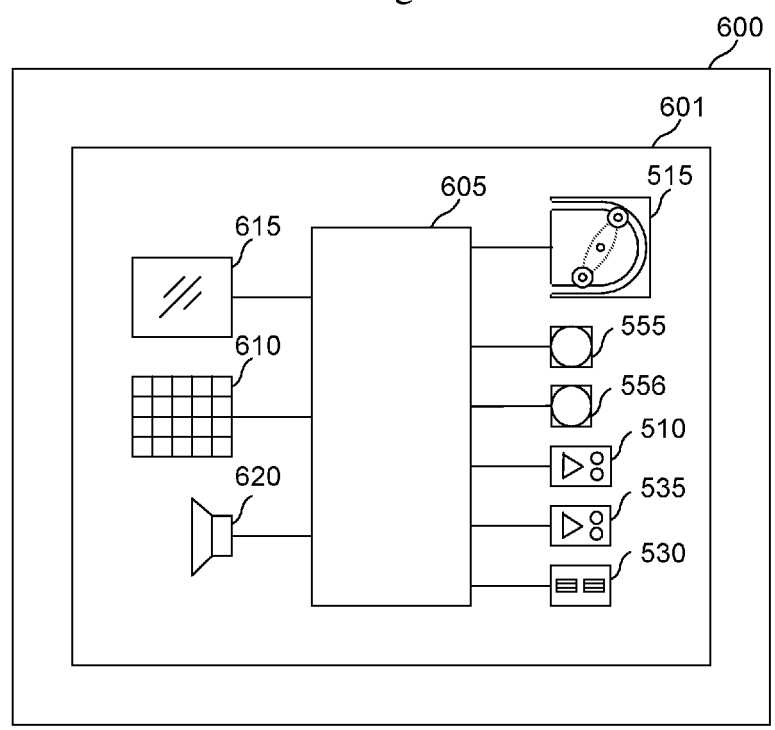
FIG. 6 shows a schematic diagram of a treatment control monitor of an embodiment of the present invention.

FIG. 6 shows a schematic diagram of a treatment control monitor 600 of an embodiment of the present invention. The treatment control monitor 600 together with the disposable extracorporeal blood circuit (for example as is shown in FIG. 5) forms the apparatus for extracorporeal blood treatment. The treatment control monitor 600 comprises a control unit 605 which is connected to an input device 610 (e.g. a key-pad), a display 615 (e.g. a LCD), and an acoustic device 620 (e.g. a buzzer or a loudspeaker). The control unit is also connected to a blood pump 515, a first pressure sensor 555, a second pressure sensor 556, a withdrawal line clamp 510, a return line clamp 535, and a blood detector 530.

The control unit 605 may comprise one or several micro processors with customary peripheral elements such as memory and data transfer circuits and/or is built on logic circuits. The control unit 605 may be designed to have redundancy and/or surveillance functionalities. The control unit 605 further comprises customary interface circuits for interacting with the connected devices. For example, amplifiers, A/D and D/A converters, power drivers, and, if the blood pump is a peristaltic blood pump which is driven by a step motor, a step motor driver circuit. Any programmable device is provided with appropriate software in order to implement the control units of the various embodiments of the present invention.

The input device 610 and the display 615, partly or as a whole, may be combined into one device by e.g. a touch screen. In operation, the operator enters information to the treatment control monitor 600 through the input device 610 and receives information by means of the display 615 and the acoustic device 620 (e.g. in the case of alarms).

The treatment control monitor 600 may comprise further elements such as are disclosed in relation to the treatment control monitor 100 (as shown in FIG. 1) or as is well known in the industry. Examples of such further elements are a syringe pump used for distributing an anti-coagulant substance, a treatment fluid pump for pumping the treatment fluid through the membrane device, arrangements for preparing the treatment fluid (for example from a water source and one or several dry concentrates), a holder for a venous drip chamber, one or several input ports to the pressure sensors, a membrane device holder to which the membrane device can be mounted, etc.

As is discussed above, it is important for the treatment control unit to monitor whether there is blood present in the extracorporeal blood circuit, in particular in the return line, for example when the priming stage is being performed, the actual treatment is ongoing or the blood is being returned to the patient after the actual treatment. Furthermore, it is recognized that there is always a risk that the blood detector, for example located at the return line, fails to detect blood in the extracorporeal blood circuit due to an erroneous connection of the tube or suitable portion of the extracorporeal blood circuit to the blood detector. The blood detector may also fail to detect blood correctly if it is damaged or if any functional element or associated circuits of the blood detector fails.

According to the present invention, a system 601 and a method for monitoring the presence of blood in the extracorporeal circuit is disclosed. The system 601 may be integrated wholly or in part in a treatment control unit 600 and the system 601 may share common parts with the treatment control unit 600.

According to a first embodiment of the present invention, and according to a first monitoring procedure, the control unit 605 reads a first pressure value as received by the first pressure sensor 555 and a second pressure value as received by the second pressure sensor 556. The control unit establishes a differential pressure value, for example by calculating the difference between the first and second pressure values. The control unit 605 compares the differential pressure with a threshold value and determines that blood is present in the membrane device 520 if the differential pressure exceeds a threshold value. This is possible since the differential pressure is higher when the membrane device 520 comprises blood compared to when it comprises priming liquid or replacement liquid. The control unit 605 detects the presence of blood in a portion of the extracorporeal circuit by reading the signal from the blood detector. Next, the control unit 605 compares its determination whether blood is present in the membrane device with the signal received from the blood detector 530 and generates a signal if the presence of blood as detected by the blood detector and the presence of blood as determined based on the differential pressure value do not coincide, that is, if the control unit determines that blood is present in the membrane device but the blood detector does not indicate that blood is present in the extracorporeal blood circuit (for example, return line), and/or it is determined that blood is not present in the membrane device but the blood detector indicates that blood is present in the extracorporeal blood circuit (for example, return line).

Figure 7:
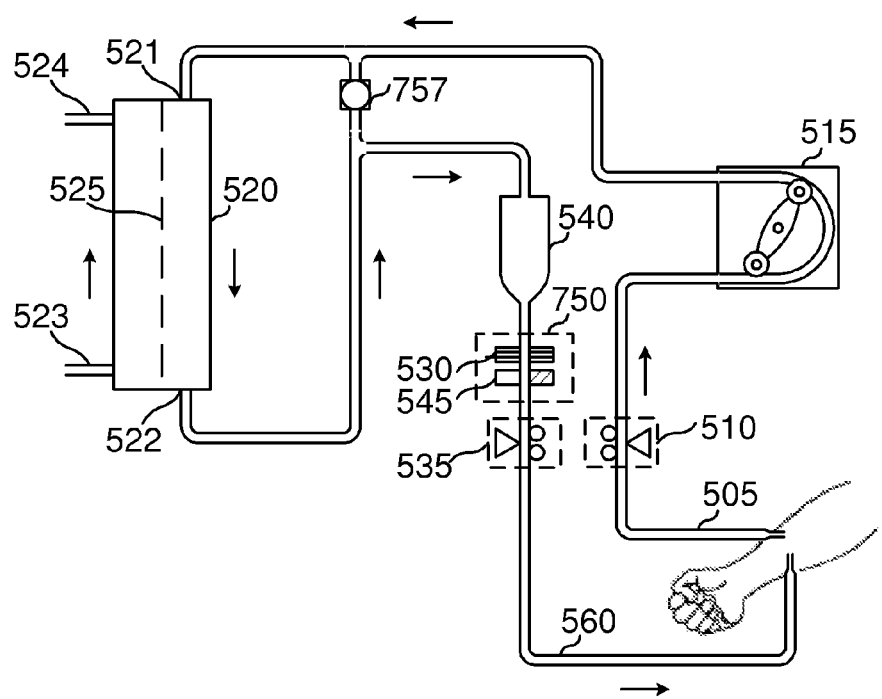
FIG. 7 shows a schematic diagram of an extracorporeal blood circuit illustrating an alternative embodiment of the present invention.

FIG. 7 shows a schematic diagram of an extracorporeal blood circuit illustrating an alternative embodiment of the present invention. The elements being identical compared to the embodiment shown in FIG. 5 have been given the same reference numbers. Instead of the first and second pressure sensors 555, 556, of FIG. 5, a differential pressure sensor 757 is connected to the withdrawal line 505 and the return line 560. The differential pressure sensor 757, which is connected to the control unit 605 (not shown) provides a signal which is representative of the differential pressure between the fluid pressure in the withdrawal line 505 and the fluid pressure in the return line 560. Additionally, in order to illustrate alternative implementations, instead of a blood detector and double clamp device 550, the withdrawal line clamp 510, and the return line clamp 535 are discrete components. Furthermore, the blood detector 530 is integrated together with at least one guiding element 545 in a blood detector device 750.

According to a second embodiment of the present invention, and according to a second monitoring procedure, the control unit 605 operates in the same manner as in the first embodiment with the difference that the control unit establishes a differential pressure value based on the value received from the differential pressure sensor 757.

Figure 8:
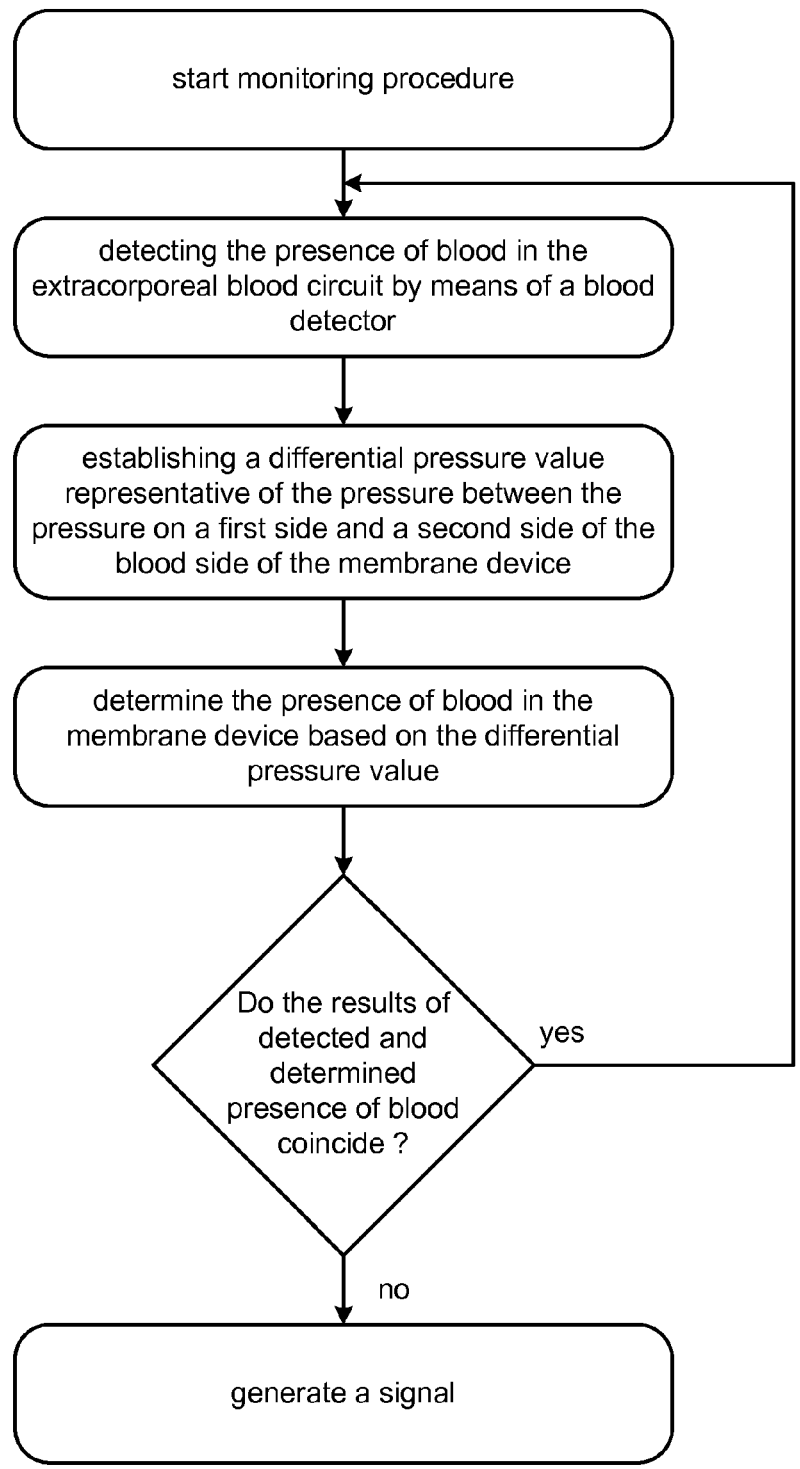
FIG. 8 shows a flow chart illustrating method steps of the first and second embodiments of the present invention.

FIG. 8 shows a flow chart illustrating method steps of the first and second embodiments.

An advantage at least of the first and second embodiments of the present invention is that the presence of blood in the extracorporeal blood circuit is determined with a high degree of certainty since two independent means and methods are used in the process. Consequently, the risks of an incorrect treatment of the patient, incorrect stop of the treatment and incorrect generation of alarms, and/or that blood from the patient may not be correctly returned to the patient, as discussed above, are significantly reduced.

According to alternative embodiments of the present invention as disclosed in the first and second embodiments, the control unit 605 determines the presence of blood in the membrane device by comparing a change of the differential pressure value (for example by deriving the differential pressure value) with a defined value.

In further embodiments, in combination with any of the disclosed embodiments, the control unit 605 prevents the generation of the signal for a period of time. Consider, for example, the situation when blood is withdrawn from the patient after the priming stage and blood is filling up the membrane device 520 by replacing the priming liquid. In this case, the differential pressure will increase and the control unit 605 will determine that blood is present in the membrane device 520. However, the blood has not yet reached the blood detector 530 (where priming liquid is still present) and the blood detector 530 will not indicate that blood is present in the return line 560 until the blood has been transported further in the return line to the blood detector 530. Similarly, in the situation when blood is returned to the patient after the actual treatment is completed and a replacement liquid is introduced in the withdrawal line 505. In this case, the differential pressure will decrease and the control unit 605 will determine that blood is not present in the membrane device 520. However, the replacement has not yet reached the blood detector 530 (where blood is still present) and the blood detector will indicate that blood is present in the return line 560 until the replacement liquid has been transported further in the return line 560 to the blood detector 530. In both these situations, as the treatment control monitor 600 is operating as it is supposed to, it is possible to avoid setting off an (incorrect) alarm in these circumstances by preventing the generation of the signal for a period of time. The period of time may be fixed (based on knowledge of how long time it normally takes for blood to be transported from the membrane device 520 to the blood detector). Alternatively, the control unit 605 may calculate the period of time based on other data. For example, the control unit 605 may determine the speed of the fluid within the extracorporeal blood circuit based on data from a fluid flow meter (not shown) and thereafter adapt the period of time based on the determined speed (for example, dividing the distance blood needs to travel from the membrane device to the blood detector with the speed, possibly multiplied with a factor in order to achieve a suitable margin). In another example, the control unit 605 may use the speed of the pump (e.g. number of steps taken by the step motor which drives the blood pump) in order to estimate the speed of the fluid and from that calculating the period time.

In further alternative embodiments, in combination with any of the disclosed embodiments, the control unit 605 does only generate the signal if the control unit 605 determines that blood is present in the membrane device 520 but the blood detector 530 does not indicate that blood is present in the extracorporeal blood circuit (for example, return line). In these embodiments, it could often be assumed that the portion of the extracorporeal blood circuit to be received by the blood detector (e.g. a tube) has not been properly connected. In this case the system 601 may be referred to as a system for determining the proper or correct connection of a portion (for example a tube) of an extracorporeal blood circuit to be received by the blood detector and corresponding method is thereby achieved.

An advantage at least of the latter embodiments of the present invention is that the proper connection of the extracorporeal blood circuit to the blood detector can be determined with a degree of certainty and, consequently, the risks of an incorrect treatment of the patient, incorrect stop of the treatment and incorrect generation of alarms, and/or that blood from the patient may not be correctly returned to the patient, as discussed above, are significantly reduced.

In yet further alternative embodiments, in combination with any of the disclosed embodiments, the control unit 605 may test the functional elements (for example, in the case the functional elements uses light, by turning the light source on and off and monitor whether the light detector responds accordingly) of the blood detector 530 before blood is allowed to enter the extracorporeal blood circuit at the position where the blood detector 530 is located. This should generally be done before the actual treatment is initiated which could be before, during or after the priming stage. Alternatively, testing is initiated based on input from the input device 610. The control unit 605 will then only initiate the monitoring procedure if the testing of the functional elements of the blood detector 530 shows that they are operating correctly. If not, then a blood detector alarm signal is generated (for example by means of the display 615 and/or acoustic device 620).

Figure 9:
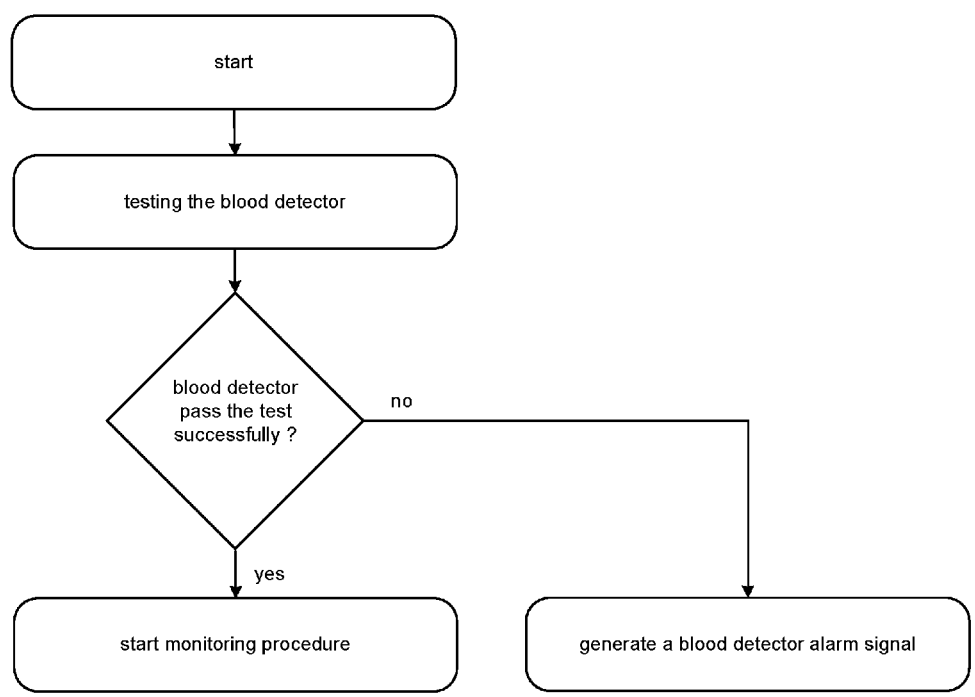
FIG. 9 shows a flow chart illustrating method steps of an alternative embodiment of the present invention.

FIG. 9 shows a flow chart illustrating method steps of the aforementioned embodiment. The box containing the text "start monitoring procedure" refers to the method illustrated in FIG. 8.

Especially in the case where the control unit 605 determines that blood is present in the membrane device 520 but the blood detector 530 does not indicate that blood is present in the extracorporeal blood circuit (for example, return line), by having tested the functional elements of the blood detector 530 prior to initiating the actual treatment, it is likely that the signal has been generated due to an erroneous connection of a portion of the extracorporeal blood circuit (for example, return line) to the blood detector 530.

An advantage at least of the latter embodiments of the present invention is that the proper connection of the extracorporeal blood circuit to the blood detector can be determined with high degree of certainty and, consequently, the risks of an incorrect treatment of the patient, incorrect stop of the treatment and incorrect generation of alarms, and/or that blood from the patient may not be correctly returned to the patient, as discussed above, are significantly reduced.

In further embodiments, in combination with any of the above embodiments, the generated signal may be used to trigger an alarm to the operator by means of the display 615 and/or the acoustic device 620. Furthermore, the signal may be used internally by the control unit 605 in order to control the treatment control monitor 600, for example by stopping the blood pump 515 and/or closing the withdrawal line clamp 510 and/or the return line clamp 535.

In alternative embodiments some of the method steps set out above may be carried out in a different sequence without departing from the present invention. Furthermore, the method steps of the various embodiments of the present invention may be used to control a monitor for extracorporeal blood treatment.

Generally, it should be understood that the pressure of the liquid in the withdrawal line may be measured in alternative locations, e.g. close to the membrane device (systemic pressure), close to the blood pump or even on the patient's side of the blood pump (on either side of the withdrawal line clamp). Similarly, the pressure of the liquid in the return line may be measured in alternative locations, e.g. close to the membrane device, close to the venous drip chamber or on either side of the blood detector and the return line clamp. Generally, these locations are referred to as the first side of the blood side of the membrane device and the second side of the blood side of the membrane device.

Furthermore, the present invention may be used in different mode of operations, including modes based on single needle access.

Aspects of some embodiments of the invention are further disclosed in the following clauses:

Clause 1. A system for determining the proper connection of a portion of an extracorporeal blood circuit to a blood detector comprising:
the blood detector (530) configured to receive the portion of the extracorporeal blood circuit and to detect the presence of blood in the received portion;
pressure sensor means (555, 556; 757) configured to provide a differential pressure value which represents the pressure between the pressure on a first side of the blood side of a membrane device and the pressure on a second side of the blood side of the membrane device;
a control unit (605) connected to the blood detector and the pressure sensor means;
characterized in that
the control unit (605) is configured to determine the presence of blood in the membrane device based on the differential pressure value; and
the control unit (605) is configured to generate a signal if the control unit has determined the presence of blood in the membrane device but the blood detector does not indicate that blood is present in the extracorporeal blood circuit.

Clause 2. A system according to clause 1 wherein the pressure sensor means comprises:
a first pressure sensor (555) configured to measure a first pressure value on a first side of the blood side of the membrane device;
a second pressure sensor (556) configured to measure a second pressure value on a second side of the blood side of the membrane device;
the first and second pressure sensors (555, 556) being connected to the control unit (605); and
the control unit (605) is configured to calculate the differential pressure value by calculating the difference between the first and second pressure values.

Clause 3. A system according to clause 1 or clause 2 wherein the control unit is configured to determine the presence of blood in the membrane device by detecting a defined change of the differential pressure value.

Clause 4. A system according to clause 1 or clause 2 wherein the control unit is configured to determine the presence of blood in the membrane device by detecting whether the differential pressure value exceeds a threshold value.

Clause 5. A system according to any one of the preceding clauses wherein the control unit is configured to prevent the generation of the signal for a period of time.

Clause 6. A system according to clause 5 wherein the control unit is configured to prevent the generation of the signal dependent on the speed of a fluid within the extracorporeal blood circuit.

Clause 7. A system according to any one of the preceding clauses wherein the system is integrated in a treatment control monitor (600) for dialysis treatment.

Clause 8. A system according to any one of the preceding clauses wherein the control unit is configured not to generate the signal if presence of blood is detected by the blood detector and presence of blood in the membrane device is not determined.

Clause 9. A system according to any one of the preceding clauses wherein the signal is indicative of that the portion of the extracorporeal blood circuit has not been properly connected to the blood detector.

Clause 10. A system according to any one of the preceding clauses further characterised in that:
the control unit is configured to test the functional elements of the blood detector before blood is allowed to enter the extracorporeal blood circuit at the position where the blood detector is located; and
the control unit is configured to determining the proper connection of a portion of an extracorporeal blood circuit to a blood detector if the testing does conclude the correct operation of the functional elements and, otherwise, the control unit is configured to generate a blood detector alarm signal.

Clause 11. A method of determining the proper connection of a portion of an extracorporeal blood circuit to a blood detector comprising the steps of:
detecting the presence of blood in a portion of the extracorporeal blood circuit by means of a blood detector;
establishing a differential pressure value which is representative of the pressure between the pressure on a first side of the blood side of a membrane device and the pressure on a second side of the blood side of the membrane device;
determine the presence of blood in the membrane device based on the differential pressure value;
generating a signal if the presence of blood in the membrane device has been determined but blood in a portion of the extracorporeal blood circuit has not been detected by means of the blood detector.

Clause 12. A method according to clause 11 wherein the step of establishing the differential pressure value comprises the steps of:
measuring a first pressure value on the first side of the blood side of the membrane device;
measuring a second pressure value on the second side of the blood side of the membrane device; and
calculate the differential pressure value by calculating the difference between the first and the second pressure values.

Clause 13. A method according to clause 11 or clause 12 wherein the step of determine the presence of blood in the membrane device comprises the step of detecting a defined change of the differential pressure value.

Clause 14. A method according to clause 11 or clause 12 wherein the step of determine the presence of blood in the membrane device comprises the step of detecting whether the differential pressure value exceeds a threshold value.

Clause 15. A method according to any one of clause 11 to clause 14 wherein further comprising the step of preventing the generation of the signal for a period of time.

Clause 16. A method according to clause 15 wherein the step of preventing the generation of the signal for a period of time further comprises the steps of:
determining the speed of a fluid within the extracorporeal blood circuit; and
adapting the time of the prevention of the generation of the signal depending on the determined speed of the fluid.

Clause 17. A method according to any one of clause 11 to clause 16 wherein the step of generating a signal is not carried out if presence of blood is detected by the blood detector but presence of blood in the membrane device is not determined.

Clause 18. A method according to any one of clause 11 to clause 17 wherein the signal is indicative of that the portion of the extracorporeal blood circuit has not been properly connected to the blood detector.

Clause 19. A method according to any one of clause 11 to clause 18 further comprising:
testing the functional elements of the blood detector before blood is allowed to enter the extracorporeal blood circuit at the position where the blood detector is located; and
determining the proper connection of a portion of an extracorporeal blood circuit to a blood detector if the testing does conclude the correct operation of the functional elements and, otherwise, generating a blood detector alarm signal.

The invention claimed is:

1. A system for monitoring the presence of blood in an extracorporeal blood circuit according to a monitoring procedure comprising:
a blood detector configured to (i) receive a portion of the extracorporeal blood circuit and (ii) generate a blood presence signal indicative of whether the presence of blood has been detected in the received portion;
a pressure sensor configured to provide a differential pressure value which represents the pressure between the pressure on a first side of a blood side of a membrane device in the blood circuit and the pressure on a second side of the blood side of the membrane device; and
a control unit connected to the blood detector and the pressure sensor, wherein the control unit is configured to (a) determine the presence of blood in the membrane device based on the differential pressure value,
(b) receive the blood presence signal from the blood detector, (c) determine if the blood presence signal coincides with the determination of the presence of blood in the membrane device based on the differential pressure value, and (d) generate a signal if the determination of (c) is that the blood presence signal does not coincide with the determination of the presence of blood in the membrane device based on the differential pressure value.

2. A system for monitoring the presence of blood according to claim 1 wherein the pressure sensor comprises:
a first pressure sensor configured to measure a first pressure value on a first side of the blood side of the membrane device;
a second pressure sensor configured to measure a second pressure value on a second side of the blood side of the membrane device;
the first and second pressure sensors being connected to the control unit; and
the control unit is configured to calculate the differential pressure value by calculating the difference between the first and second pressure values.

3. A system for monitoring the presence of blood according to claim 1 wherein the control unit is configured to determine the presence of blood in the membrane device by detecting a defined change of the differential pressure value.

4. A system for monitoring the presence of blood according to claim 1 wherein the control unit is configured to determine the presence of blood in the membrane device by detecting whether the differential pressure value exceeds a threshold value.

5. A system for monitoring the presence of blood according to claim 1 wherein the control unit is configured to prevent the generation of the signal for a period of time.

6. A system for monitoring the presence of blood according to claim 5 wherein the control unit is configured to prevent the generation of the signal dependent on the speed of a fluid within the extracorporeal blood circuit.

7. A system for monitoring the presence of blood according to claim 1 wherein the system is integrated in a treatment control monitor for dialysis treatment.

8. A system for monitoring the presence of blood according to claim 1 wherein the control unit is configured not to generate the signal if presence of blood is detected by the blood detector and presence of blood in the membrane device is not determined.

9. A system for monitoring the presence of blood according to claim 1 wherein:
the control unit is configured to test at least one functional element of the blood detector before blood is allowed to enter the extracorporeal blood circuit at the position where the blood detector is located; and
the control unit is configured to initiate the monitoring procedure if the testing does conclude the correct operation of the functional elements and, otherwise, the control unit is configured to generate a blood detector alarm signal.

10. A method of monitoring the presence of blood in an extracorporeal blood circuit according to a monitoring procedure comprising:
generating a blood presence signal indicative of whether the presence of blood has been detected in a portion of the extracorporeal blood circuit by a blood detector;
establishing a differential pressure value which is representative of the pressure between the pressure on a first side of the blood side of a membrane device and the pressure on a second side of the blood side of the membrane device;
determining the presence of blood in the membrane device based on the differential pressure value;
determining if the blood presence signal coincides with the determination of the presence of blood in the membrane device based on the differential pressure value; and
generating a signal if the determination is that the blood presence signal does not coincide with the determination of the presence of blood in the membrane device based on the differential pressure value.

11. A method of monitoring the presence of blood according to claim 10 wherein the step of establishing the differential pressure value comprises:
measuring a first pressure value on the first side of the blood side of the membrane device;
measuring a second pressure value on the second side of the blood side of the membrane device; and
calculating the differential pressure value by calculating the difference between the first and the second pressure values.

12. A method of monitoring the presence of blood according to claim 10 wherein the step of determining the presence of blood in the membrane device comprises the step of detecting a defined change of the differential pressure value.

13. A method of monitoring the presence of blood according to claim 10 wherein the step of determining the presence of blood in the membrane device comprises the step of detecting whether the differential pressure value exceeds a threshold value.

14. A method of monitoring the presence of blood according to claim 10 wherein further comprising preventing the generation of the signal for a period of time.

15. A method of monitoring the presence of blood according to claim 14 wherein the step of preventing the generation of the signal for a period of time further comprises:
   determining the speed of a fluid within the extracorporeal blood circuit; and
   adapting the time of the prevention of the generation of the signal depending on the determined speed of the fluid.

16. A method of monitoring the presence of blood according to claim 10 wherein the step of generating a signal is not carried out if presence of blood is detected by the blood detector but presence of blood in the membrane device is not determined.

17. A method of monitoring the presence of blood according to claim 10 further comprising:
   testing the functional elements of the blood detector before blood is allowed to enter the extracorporeal blood circuit at the position where the blood detector is located; and
   initiating the monitoring procedure if the testing does conclude the correct operation of the functional elements and, otherwise, generating a blood detector alarm signal.

18. A system to monitor blood in an extracorporeal blood circuit including a blood passage and a membrane device having a blood side included in the blood passage, the system comprising:
   a blood detector configured to receive a portion of the blood passage in the extracorporeal blood circuit and configured to generate blood presence data indicating whether blood is in the received portion of the blood passage;
   a pressure sensor system configured to provide differential pressure data indicating a pressure difference between an inlet and an outlet of the blood side of the membrane device;
   a control unit using the differential pressure data and the blood presence data, the control unit including a non-transitory memory and a processor executing instructions stored in the memory, wherein the instructions cause the control unit to:
   (a) determine the presence of blood in the blood side of the membrane device based on the differential pressure data,
   (b) receive the blood presence data from the blood detector,
   (c) determine if the blood presence data indicates the presence of blood while the differential pressure data indicates an absence of blood, and
   (d) generate an action if the determination of (c) is that the blood presence data indicates the presence of blood while the differential pressure data indicates an absence of blood.

19. The system of claim 18 wherein the action is at least one of an alarm and ceasing blood flow through the blood passage.

20. The system of claim 18 wherein the pressure sensor system comprises:
   a first pressure sensor configured to measure a first pressure value in the blood passage connected to the inlet to the blood side of the membrane device, and
   a second pressure sensor configured to measure a second pressure value in the blood passage connected to the outlet of the blood side of the membrane device;
   wherein the control unit receives the first pressure value and the second pressure value and the instructions cause the control unit to calculate the differential pressure value based on the first and second pressure values.

21. The system of claim 18 wherein the instructions causing the control unit to determine the presence of blood in the membrane device based on the differential pressure data further causes the control unit to detect a defined change of the differential pressure value in a succession of differential pressure data.

22. The system of claim 18 wherein the instructions causing the control unit to determine the presence of blood in the membrane device based on the differential pressure data further causes the control unit to determine whether the differential pressure value exceeds a threshold value.

23. The system of claim 18 wherein the instructions cause the control unit to prevent generation of the predetermined action for a determined period.

24. The system of claim 23 wherein the determined period is determined based on a speed of fluid flow through the blood passage.

25. The system of claim 18 wherein the system is integrated in a treatment control monitor for dialysis treatment.

26. The system of claim 18 wherein the instructions cause the control unit to prevent generation of the predetermined action if presence of blood is detected by the blood detector and determination of the presence of blood in the membrane device in that there is no determination of whether there is or is not blood in the membrane device.

27. The system of claim 18 wherein the instructions cause the control unit to:
   test the blood detector before blood flows through the portion of the blood passage received by the blood detector, and
   prevent blood flow through the blood passage and generate a blood detector alarm signal if the blood detector fails the test.

28. The system of claim 1, wherein the control unit is further configured to generate a signal only if the determination of (c) is that the blood detection signal does not coincide with the determination of the presence of blood based on the differential pressure value.

* * * * *